United States Patent [19]
Kinoshita et al.

[11] Patent Number: 5,697,919
[45] Date of Patent: Dec. 16, 1997

[54] PORTABLE ANALGESIC SYSTEM

[75] Inventors: Kodai Kinoshita, Tokyo; Osamu Tsukada, Nagano-ken, both of Japan

[73] Assignee: Tsukada Medical Research Co., Ltd., Tokyo, Japan

[21] Appl. No.: 406,944

[22] PCT Filed: Apr. 11, 1994

[86] PCT No.: PCT/JP94/00608

§ 371 Date: Mar. 24, 1995

§ 102(e) Date: Mar. 24, 1995

[87] PCT Pub. No.: WO95/27521

PCT Pub. Date: Oct. 19, 1995

[51] Int. Cl.$^6$ .................................................. A61M 5/00
[52] U.S. Cl. ........................................ 604/248; 604/185
[58] Field of Search ......................... 604/30, 32, 48, 604/212, 216, 246, 248, 264, 280, 37, 181, 185, 214, 217

[56] References Cited

U.S. PATENT DOCUMENTS

| | | |
|---|---|---|
| 3,468,308 | 9/1969 | Bierman . |
| 5,002,528 | 3/1991 | Palestrant ........................ 604/28 |
| 5,053,012 | 10/1991 | Edwards et al. . |
| 5,061,243 | 10/1991 | Winchell et al. ................ 604/132 |
| 5,211,632 | 5/1993 | Tsukada ........................... 605/132 |
| 5,360,411 | 11/1994 | Mimura et al. .................. 604/246 |
| 5,439,452 | 8/1995 | McCarty ........................... 604/248 |

FOREIGN PATENT DOCUMENTS

| | | |
|---|---|---|
| 0295504 | 12/1988 | European Pat. Off. . |
| 0452912 | 10/1991 | European Pat. Off. . |
| 0473781 | 3/1992 | European Pat. Off. . |
| 0509754 | 10/1992 | European Pat. Off. . |

*Primary Examiner*—Corrine M. McDermott
*Attorney, Agent, or Firm*—Sughrue, Mion, Zinn, Macpeak & Seas, PLLC

[57] ABSTRACT

A portable analgesic system comprises: a continuous injector (1) for liquid medicine which discharges liquid medicine continuously for a given period of time; a switch valve (2) connected to an outlet of the injector for shutting off discharge of liquid medicine from the injector (1); a three-way connector (3) to an outlet of the switch valve (2) and having three ways; a flexible reservoir (4) connected to one way of the three-way connector for storing liquid medicine; and a pressure-check valve (5) connected to another way of the three-way connector for opening a flow passage only when a pressure of liquid medicine in the reservoir rises over a given value.

3 Claims, 4 Drawing Sheets

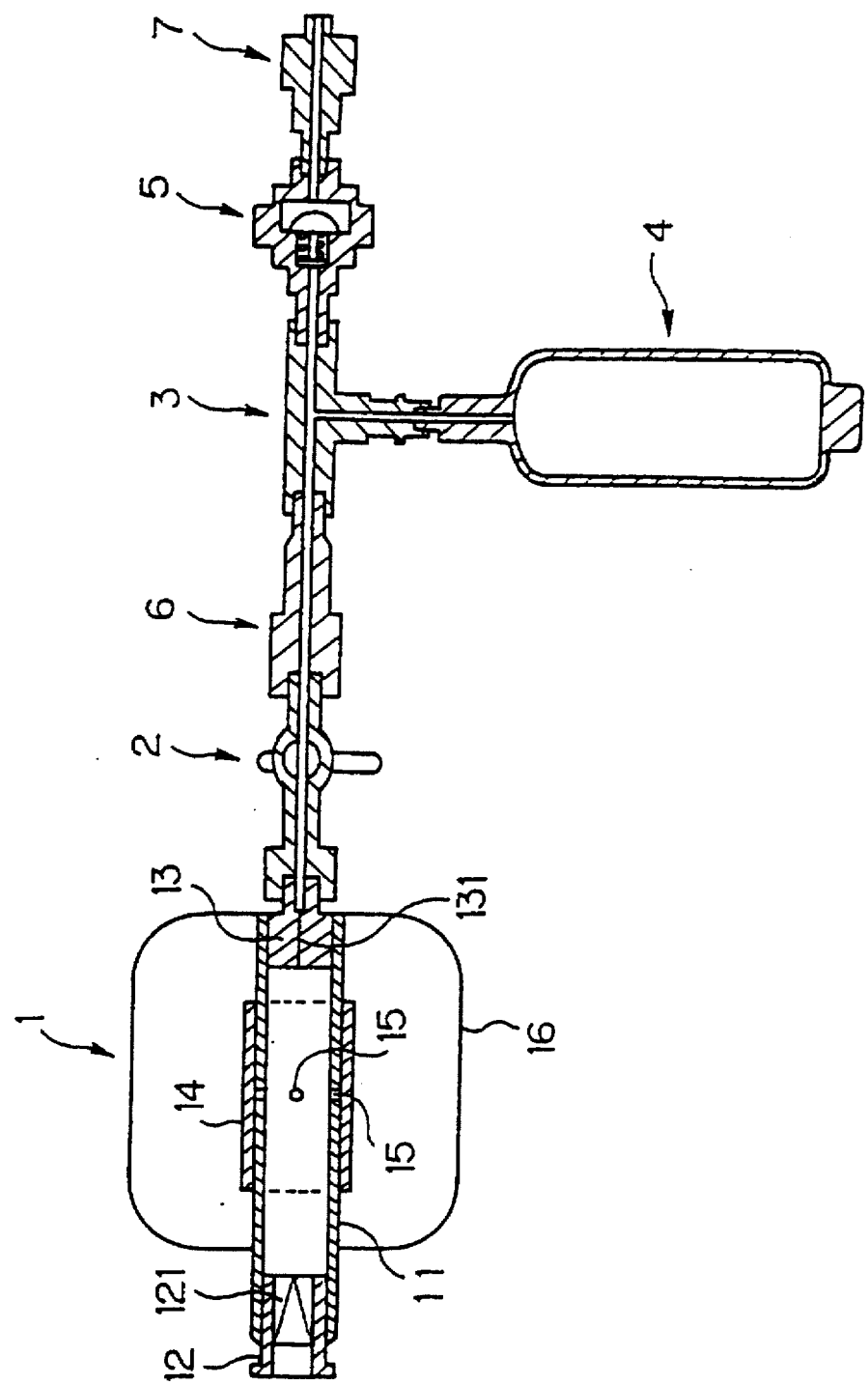

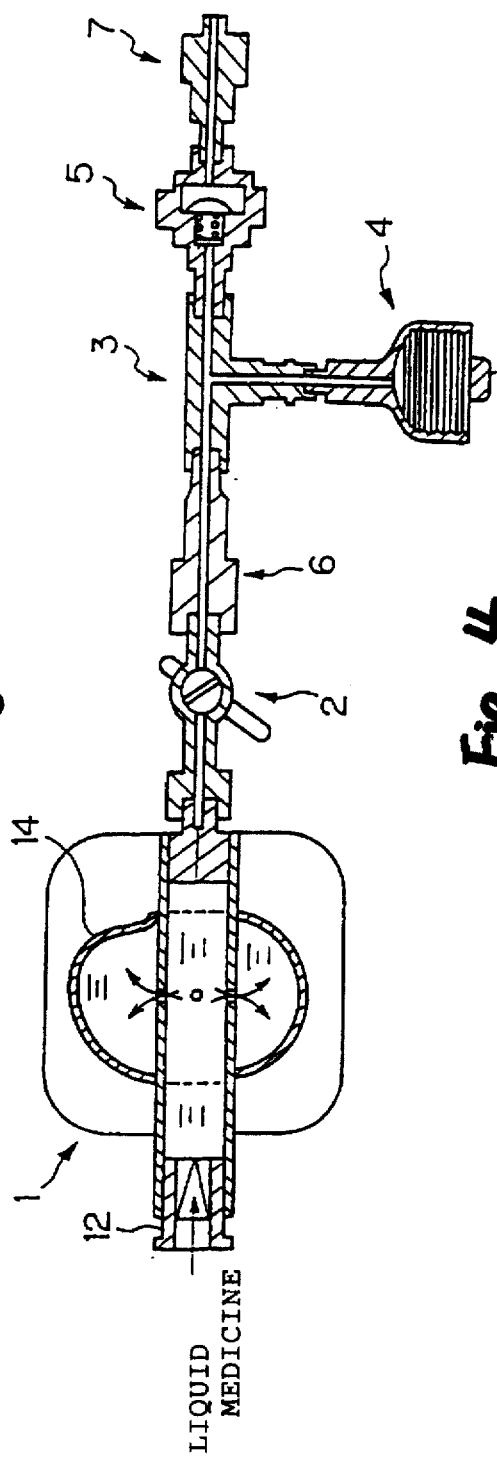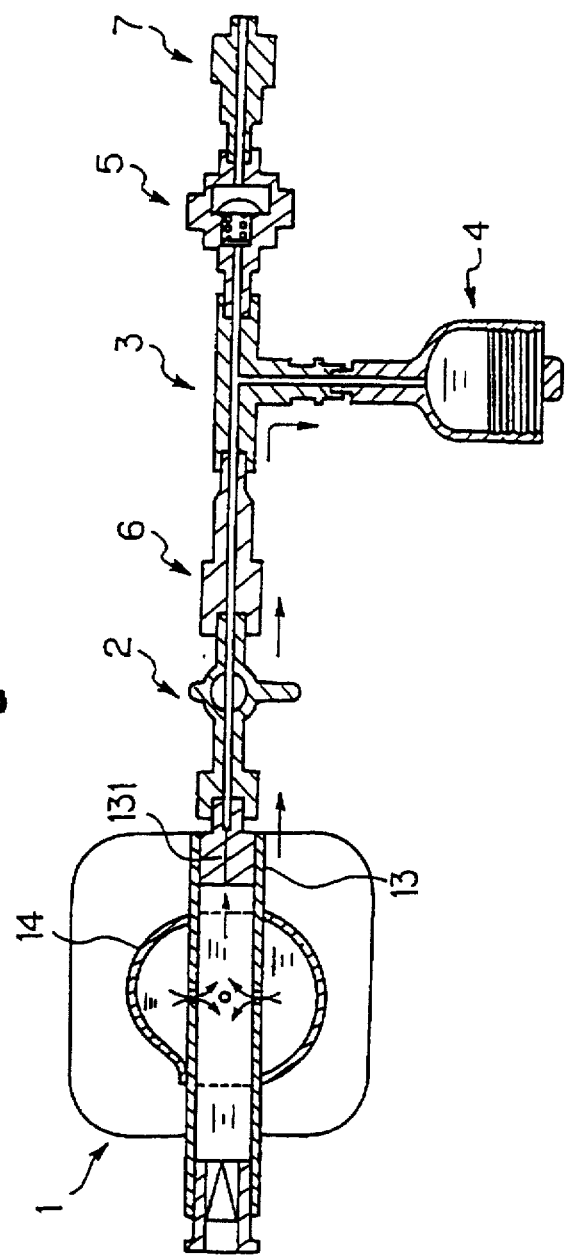

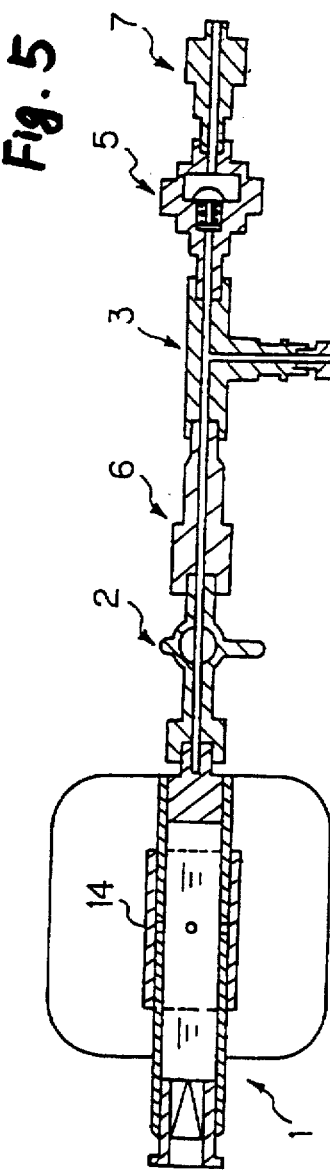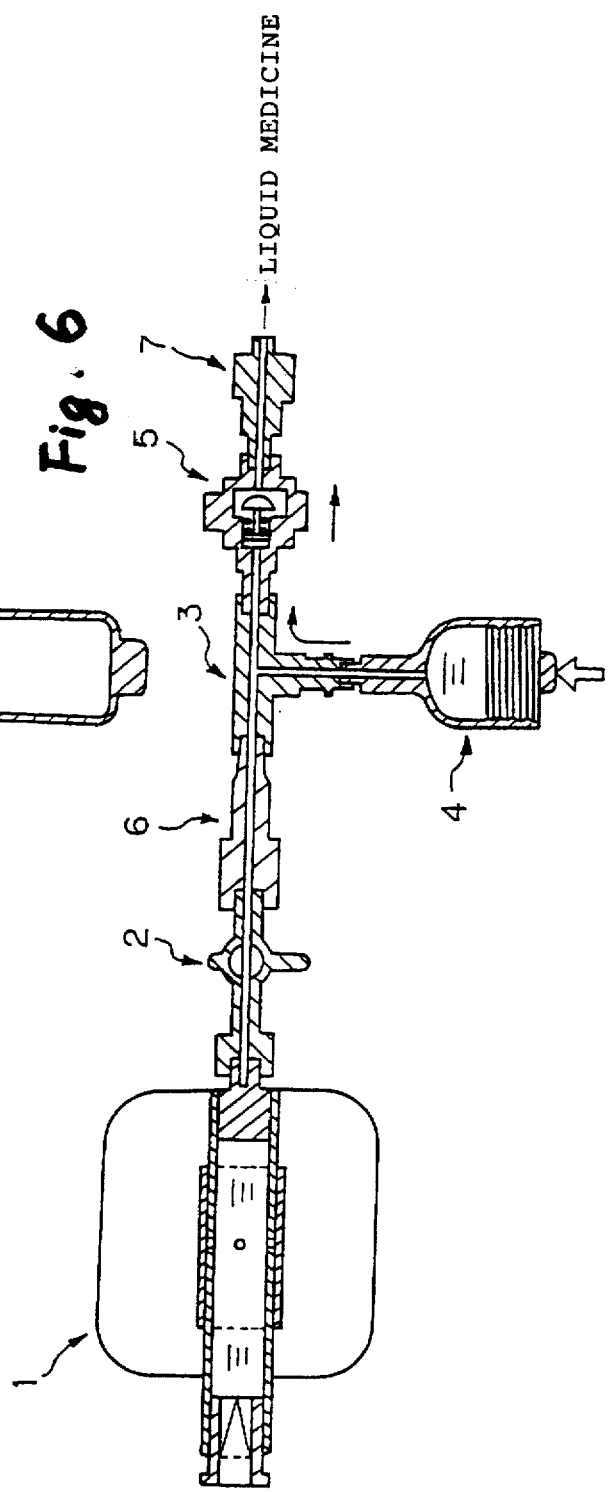

PORTABLE ANALGESIC SYSTEM

BACKGROUND OF THE INVENTION

1. Field of the Invention

This invention relates to a portable analgesic system which is attached to a patient's body.

2. Background

Analgesics play an important role in pain control and in cases involving chronic pain. It has heretofore been necessary for a patient to be hospitalized or visit a hospital as an out-patient for a long time.

The need for frequent injection of liquid medicine such as an analgesic or the like is onerous both to a patient and in terms of time and efficiency to a hospital. Consequently, an automatic injection system has been developed which injects liquid medicine to an in-patient periodically and automatically. However, conventional systems are large in size and expensive and physically limit a patient.

Thus, a convenient automatic injection system which is not physically limiting and can be applied to in-patients, out-patients, and home-patients has been desired for a long time.

SUMMARY OF THE INVENTION

An object of the present invention is to provide a portable and convenient analgesic system which is attached to a patient's body and can inject liquid medicine into the patient's body as required by a patient.

In order to achieve the above object, a portable analgesic system comprises: a continuous injector for liquid medicine which discharges liquid medicine continuously for a given period of time; a switch valve connected to an outlet of said injector for shutting off discharge of liquid medicine from said injector; a three-way connector to an outlet of said switch valve and having three ways; a flexible reservoir connected to one way of said three-way connector for storing liquid medicine; and a pressure-check valve connected to another way of said three-way connector for opening a flow passage only when a pressure of liquid medicine in said reservoir rises above a given value.

In the portable analgesic system of the present invention, a continuous injector for liquid medicine which has a given capacity and a given self-maintaining discharge time is prepared beforehand and a given kind and amount of liquid medicine is injected into the injector in compliance with the condition of a patient. Then, the switch valve is opened to transfer liquid medicine to the reservoir for a given period of time. During this transferring period the patient can freely move with the system being attached to one's body.

A period of time for transferring liquid medicine from the injector to the reservoir coincides with a self-maintaining remedy effect time of liquid medicine. When the patient feels pain, the patient compresses the reservoir to inject the liquid medicine contained in the reservoir into one's body through the pressure-check valve.

Preparing for a next pain, the injector can then be supplied with liquid medicine by a licensee at the patient's home or a hospital.

BRIEF DESCRIPTION OF DRAWINGS

FIG. 2 is a longitudinal cross sectional view of the system taken along line II—II in FIG. 1;

FIG. 3 is an explanatory view illustrating an operation of injecting liquid medicine into a continuous injector for liquid medicine;

FIG. 4 is an explanatory view illustrating an operation of transferring the liquid medicine from the injector to a reservoir;

FIG. 5 is an explanatory view of operation at a finished state of transferring of the liquid medicine to the reservoir; and FIG. 6 is an explanatory view illustrating an operation of ejecting the liquid medicine out of the system upon compressing the reservoir.

DETAILED DESCRIPTION OF THE INVENTION

Figure 1:
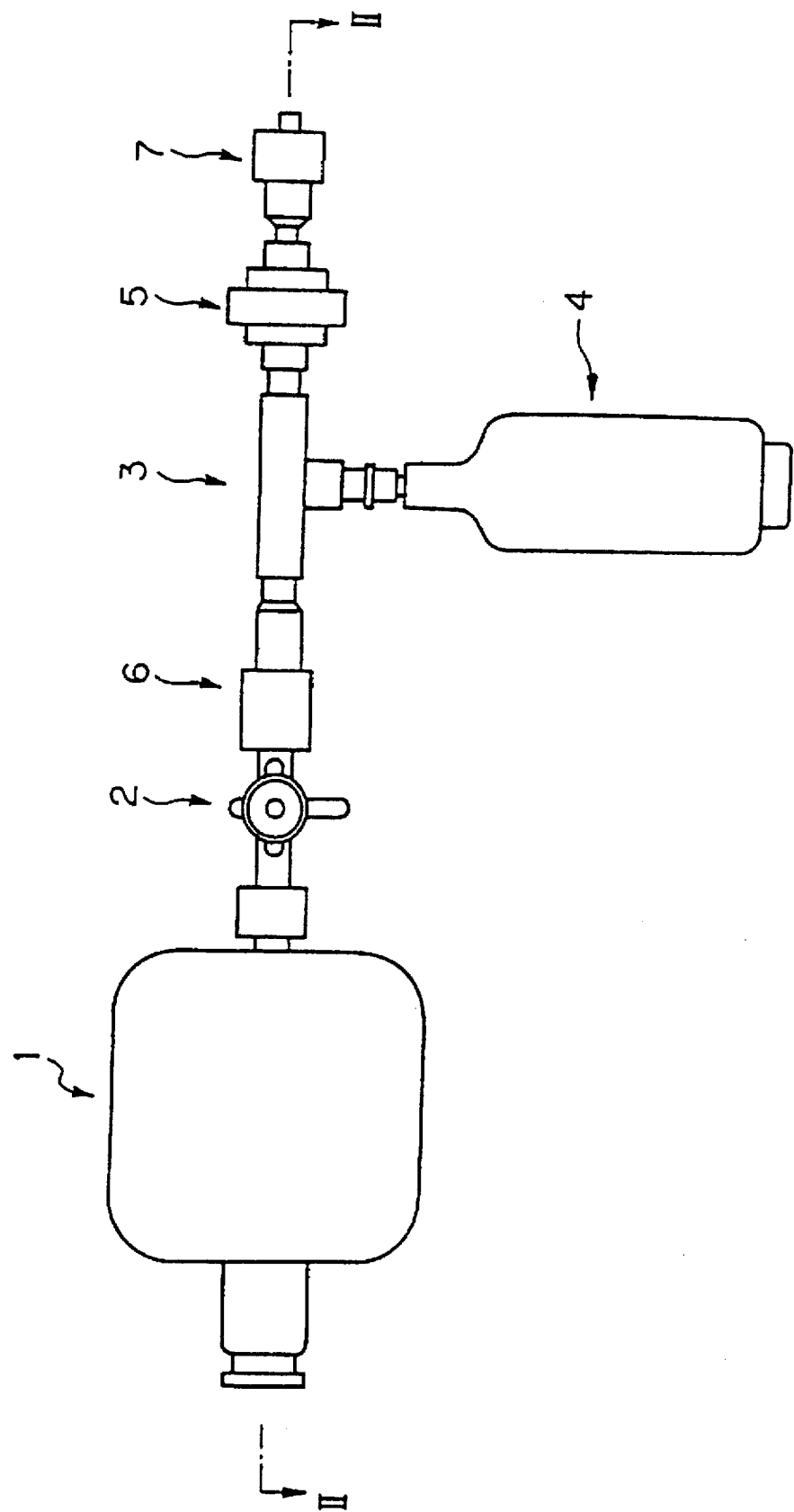
FIG. 1 is a plan view of a portable analgesic system of the present invention.

An embodiment of a portable analgesic system of the present invention will be explained below by referring now to FIGS. 1 through 6.

As shown in FIGS. 1 and 2, a portable analgesic system of the present invention comprises: a continuous injector 1 for liquid medicine which discharges liquid medicine continuously for a given period of time; a switch valve 2 connected to an outlet of the injector 1 for shutting off discharge of liquid medicine from the injector 1; a three-way connector 3 connected to an outlet of the switch valve 2 and having three ways; a flexible reservoir 4 connected to one way of the three-way connector for storing liquid medicine; and a pressure-check valve 5 connected to another way of the three-way connector 3 for opening a flow passage only when a pressure of liquid medicine in the reservoir 4 rises above a given value.

Preferably, the switch valve 2 and three-way connector 3 are coupled through a female luer connector 6 to each other while a male luer connector 7 is connected to an outlet of the pressure-check valve 5. The female luer connector 6 assures the formation of a space for enabling easy operation of the switch valve 2. The male luer connector 7 enables easy connection of a catheter and the like to the system.

The present application has developed an appropriate continuous injector 1 as disclosed in Japanese Patent No. 1384289. This injector includes an inlet portion for receiving liquid medicine, an outlet portion for discharging liquid medicine, and a balloon which connects the inlet portion to the outlet portion. Liquid medicine injected in the balloon flows out through the outlet portion for a long period of time.

With reference to FIG. 2, the continuous injector 1 is provided on opposite ends of a cylindrical body 11 with an inlet portion 12 and an outlet portion 13. A balloon 14 is attached to an outer periphery of the cylindrical body 11. An interior of the balloon 14 is communicated with an interior of the cylindrical body 11 through a communication hole 15.

The cylindrical body 11 may be omitted and the inlet portion 12 and outlet portion 13 may be directly interconnected.

The inlet portion 12 is provided with a check valve 121 which prevents injected liquid medicine from flowing in a reverse direction. The balloon 14 is made of an elastic material and can accommodate a given amount of liquid medicine. The outlet portion 13 is provided with a control path 131 which controls an outflow period of time for the liquid medicine.

In order to protect the balloon 14, when inflated against an external force, a safety cover 16 is attached to the injector 1.

The switch valve 2, female luer connector 6, three-way connector 3, and male luer connector 7 can be made from products already on the market.

The reservoir 4 is made of a durable and flexible material (for example, polyethylene, polypropylene, and the like) and formed into a ball, circle, bellows shape, or the like. The reservoir 4 is detachably attached to the three-way connector 3 in preparation for breakage, pollution, or the like.

The pressure-check valve 5 is preferably, for example, made from an umbrella valve on the market. The umbrella valve is closed normally and opened when an internal pressure rises over a given value, for example, about 250 mm Hg. This pressure-setting does not actuate the umbrella valve under an injection pressure of liquid medicine to the reservoir 4 (about 100–200 mm Hg) but is below a pressure caused upon compression of the reservoir 4 which is filled with liquid medicine (about 350–400 mm Hg).

Next, an operation of the portable analgesic system of the present invention will be explained by referring to FIGS. 3 through 6.

First, as shown in FIG. 3, the switch valve 2 is closed, the reservoir 4 is compressed to the minimum volume, and a given amount of liquid medicine (for example, physiological saline, grape sugar, antibiotic substance, calmative, analgesic, heparin, nitroglycerin solution and the like) is injected into the continuous injector 1 through the inlet portion 12 by an injector or the like.

The capacity and discharge-maintaining period of time of the injector 1 is selected beforehand in accordance with the condition of the patient.

After the preparation described above, the system of the present invention is secured to the patient by connecting the male luer connector 7 to an interior of the body through a catheter or the like (not shown). Alternately, the above injection of liquid medicine may be carried out after the present system has been secured to the patient's body.

Next, as shown in FIG. 4, the switch valve 2 is opened. Liquid medicine is gradually stored in the reservoir 4 for a long period of time (for example, 0.5–10 hours) through the control path of the outlet portion 13, switch valve 2, female luer connector 6, and three-way connector 3 by means of a contraction force of the balloon 14.

Finally, as shown in FIG. 5, all of the liquid medicine in the balloon 14 is transferred to the reservoir 4. An amount of liquid medicine to be accumulated in the reservoir 4 can be adjusted by operating the switch valve 2 before the reservoir 4 is filled with liquid medicine. However, since the operation of the switch valve during transferring of liquid medicine must be carried out sometimes under a severe control of a doctor, a locking mechanism (not shown) may be provided in order to bring the switch valve into an unable state of operation during transfer.

Thereafter, when the patient feels pain, the liquid medicine can be ejected from the reservoir 4 through the three-way connector 3, pressure-check valve 5, and male luer connector 7 to the outside (interior of the patient's body) by manually compressing the reservoir by the patient, as shown in FIG. 6.

The present system can be used again by repeating the above operation.

Industrial Applicability

The system of the present invention can be applied for first-aid treatment as well as in chronic conditions including terminal care. Also, it can be applied for sedation, detoxification, fever control, supply of nutrition, and the like as well as for analgesics.

We claim:

1. A portable analgesic system, comprising:
   an injector including a balloon in which a liquid medicine is disposed, said injector having an injector outlet;
   a switch valve connected to said injector outlet for preventing discharge of the liquid medicine;
   a three-port connector including a first port, a second port and a third port, and adapted to fluidly connect two of its three ports at a time, said first port being connected to said switch valve;
   a flexible reservoir connected to said second port, said flexible reservoir being compressible by said patient; and
   a pressure valve set to a predetermined pressure and connected at one end to said third port and at another end to the patient,
   wherein said three-port connector interconnects said first and second ports such that said liquid medicine is automatically discharged from said balloon into said flexible reservoir via said injection outlet, said switch valve and said three-port connector as a result of contractive pressure applied to said balloon, and thereafter, said three-port connector interconnects said second port with said third port such that when the pressure in said reservoir exceeds said predetermined pressure the liquid medicine is supplied via said pressure valve to said patient.

2. The analgesic system of claim 1, wherein the pressure in said flexible reservoir is adjustable by said patient by manually compressing said flexible reservoir.

3. The analgesic system of claim 1, wherein said liquid medicine is gradually stored in said reservoir for a period of between 0.5 and 10 hours.

* * * * *